(12) United States Patent
Stiegler et al.

(10) Patent No.: US 7,595,049 B2
(45) Date of Patent: Sep. 29, 2009

(54) IGG1 MONOCLONAL ANTIBODY WITH ANTI-HIV NEUTRALIZING ACTIVITY

(75) Inventors: Gabriela Stiegler, Fels am Wagram (AT); Renate Kunert, Deutsch-Wagram (AT); Hermann Katinger, Vienna (AT)

(73) Assignee: Polymun Scientific Immunobiologische Forschung GmbH, Vienna (AT)

( * ) Notice: Subject to any disclaimer, the term of this patent is extended or adjusted under 35 U.S.C. 154(b) by 517 days.

(21) Appl. No.: 10/485,525

(22) PCT Filed: Sep. 9, 2002

(86) PCT No.: PCT/EP02/10070

§ 371 (c)(1),
(2), (4) Date: Mar. 18, 2004

(87) PCT Pub. No.: WO03/022879

PCT Pub. Date: Mar. 20, 2003

(65) Prior Publication Data

US 2004/0241641 A1 Dec. 2, 2004

(51) Int. Cl.
 *A61K 39/42* (2006.01)
 *C12N 5/06* (2006.01)
 *C12P 21/08* (2006.01)

(52) U.S. Cl. .............. 424/148.1; 424/160.1; 435/339.1; 530/388.35

(58) Field of Classification Search .............. 424/148.1, 424/160.1; 530/388.35
 See application file for complete search history.

(56) References Cited

U.S. PATENT DOCUMENTS 5,556,744 A 9/1996 Weiner et al.

FOREIGN PATENT DOCUMENTS

WO WO 94/29339 12/1994
WO WO 01/24810 A1 4/2001

OTHER PUBLICATIONS

D'Souza, M. P., et al., 1994, "Evaluation of monoclonal antibodies to HIV-1 envelope by neutralization and binding assays: an international collaboration", AIDS 8:169-181.*
Kunert, R., et al., 2000, "Stable recombinant expression of the anti-HIV-1 monoclonal antibody 2F5 after IgG3/IgG1 subclass switch in CHO cells", Biotech. Bioengineer. 67(1):97-103.*
Bansal, G. P., 2007, A summary of the workshop on passive immunization using monoclonal antibodies for HIV/AIDS, held at the National Institute of Allergy and Infectious Diseases, Bethesda, Mar. 10, 2006, Biol. 35:367-371.*
Trkola, A., et al., 2005, Delay of HIV-1 rebound after cessation of antiretroviral therapy through passive transfer of human neutralizing antibodies, Nat. Med. 11(6):615-622.*
Haigwood, N. L., 2004, Predictive value of primate models for AIDS, AIDS Rev. 6:187-198.*
Staprans, S. I., and M. B. Feinberg, 2004, The roles of nonhuman primates in the preclinical evaluation of candidate AIDS vaccines, Expert Rev. Vaccines 3(4):S5-S32.*
Montefiori, D. C., 2005, Neutralizing antibodies take a swipe at HIV in vivo, Nat. Med. 11(6):593-594.*
S. A. Calarota & O. V. Libonatti: "Maternal Transmission to HIV-1 Envelope Domains: No Correlation with HIV-1 Vertical Transmission in Patients from Argentina," Scand J Immunol, vol. 52, No. 3, 2000, pp. 292-297, XP-002244086.
M. B. Zwick et al.: "Broadly Neutralizing Antibodies Targeted to the Membrane-Proximal External Region of Human Immunodeficiency Virus Type 1 Glycoprotein gp41," Journal of Virology, vol. 75, No. 22, Nov. 2001, pp. 10892-10905, XP002244086.
M. P. D'Souza et al.: "Evaluation of Monoclonal Antibodies to Human Immunodeficiency Virus Type 1 Primary Isolates by Neutralization Assays: Performance Criteria for Selecting Candidate Antibodies for Clinical Trials," The Journal of Infectious Diseases, 1997, pp. 1056-1062.
A. Buchacher et al.: "Generation of Human Monoclonal Antibodies against HIV-1 Proteins; Electrofusion and Epstein-Barr Virus Transformation for Peripheral Blood Lymphocyte Immortalization," Aids Research and Human Retroviruses, vol. 10, No. 4, 1994, pp. 359-369.
D. R. Burton et al.: "Efficient Neutralization of Primary Isolates of HIV-1 by a Recombinant Human Monoclonal Antibody," Science, vol. 266, Nov. 11, 1994, pp. 1024-1027.
P. W. H. I. Parren et al.: "The Neutralizing Antibody Response to HIV-1: Viral Evasion and Escape from Humoral Immunity," AIDS, 1999, 13 (suppl A), pp. S137-S158.
M. P. D'Souza et al.: "Evaluation of Monoclonal Antibodies to HIV-1 Envelope by Neutralization and Binding Assays: An International Collaboration," AIDS, 1994, vol. 8, pp. 169-181.

(Continued)

*Primary Examiner*—Jeffrey S. Parkin
(74) *Attorney, Agent, or Firm*—Oliff & Berridge, PLC (57) ABSTRACT

The present invention relates to neutralizing anti-HIV-1 antibodies, particularly to mAb 4E10-IgG1, which has an HIV-1 neutralizing potency comparable to the one of mAb 2F5 and 2G12. 4E10-IgG1 binds to a novel conserved epitope (NWFDIT) C-terminal of the ELDKWA epitope recognized by 2F5.1 appears that both epitopes are cryptic epitopes within a region that may be accessible in a virus-cell fusion intermediate state only. 4E10-IgG1 potently neutralizes tissue culture adapted strains but also primary isolates of different clades, including A, B, C, D, and E, inclusing viruses that were found to be resistant to 2F5. None of the tested isolates was resistant to both anti-gp41-antibodies. The invention therefore also relates to peptides containing the 4E10 epitope and to compositions made thereof, as well as to anti-idiotypic antibodies that are reactive with the paratope of 4E10-IgG1, to compositions containing an antiidiotypic antibody optionally in combination with a peptide containing the 4E10 epitope, and to anti-HIV-1 compositions comprising 4E10-IgG1, optionally in combination with another neutralizing antibody such as 2F5 and/or 2G12.

10 Claims, 3 Drawing Sheets

R. Kunert et al.: "Stable Recombinant Expression of the Anti HIV-1 Monoclonal Antibody 2F5 After lgG3/lgG1 Subclass Switch in CHO Cells," Biotechnology and Bioengineering; vol. 67; vol. 1; Jan. 5, 2000; pp. 97-103.

Gabriela Stiegler et al., "A Potent Cross-Clade Neutralizing Human Monoclonal Antibody against a Novel Epitope on gp41 of Human Immunodeficiency Virus Type 1", Aids Research and Human Retroviruses, vol. 17, No. 18, pp. 1757-1765, 2001.

* cited by examiner

SEQUENCE LISTING

<160> NUMBER OF SEQ ID NOS: 17

<210> SEQ ID NO 1
<211> LENGTH: 6
<212> TYPE: PRT
<213> ORGANISM: Human immunodeficiency virus type 1

<400> SEQUENCE: 1

Asn Trp Phe Asp Ile Thr
1               5

<210> SEQ ID NO 2
<211> LENGTH: 6
<212> TYPE: PRT
<213> ORGANISM: Human immunodeficiency virus type 1

<400> SEQUENCE: 2

Asn Trp Phe Asn Ile Thr
1               5

<210> SEQ ID NO 3
<211> LENGTH: 6
<212> TYPE: PRT
<213> ORGANISM: Human immunodeficiency virus type 1

<400> SEQUENCE: 3

Ser Trp Phe Gly Ile Thr
1               5

<210> SEQ ID NO 4
<211> LENGTH: 6
<212> TYPE: PRT
<213> ORGANISM: Human immunodeficiency virus type 1

<400> SEQUENCE: 4

Thr Trp Phe Gly Ile Thr
1               5

<210> SEQ ID NO 5
<211> LENGTH: 6
<212> TYPE: PRT
<213> ORGANISM: Human immunodeficiency virus type 1

<400> SEQUENCE: 5

Asn Trp Phe Ser Ile Thr
1               5

<210> SEQ ID NO 6
<211> LENGTH: 11
<212> TYPE: PRT
<213> ORGANISM: Human immunodeficiency virus type 1

<400> SEQUENCE: 6

Leu Trp Asn Trp Phe Asp Ile Thr Asn Trp Leu
1               5                   10

<210> SEQ ID NO 7
<211> LENGTH: 20
<212> TYPE: PRT
<213> ORGANISM: Human immunodeficiency virus type 1

<400> SEQUENCE: 7

Leu Leu Glu Leu Asp Lys Trp Ala Ser Leu Trp Asn Trp Phe Asp Ile

```
                1               5                  10                  15

Thr Asn Trp Leu
            20

<210> SEQ ID NO 8
<211> LENGTH: 23
<212> TYPE: PRT
<213> ORGANISM: Human immunodeficiency virus type 1

<400> SEQUENCE: 8

Glu Gln Glu Leu Leu Glu Leu Asp Lys Trp Ala Ser Leu Trp Asn Trp
1               5                  10                  15

Phe Asp Ile Thr Asn Trp Leu
            20

<210> SEQ ID NO 9
<211> LENGTH: 11
<212> TYPE: PRT
<213> ORGANISM: Human immunodeficiency virus type 1

<400> SEQUENCE: 9

Asp Ile Thr Asn Trp Leu Trp Tyr Ile Lys Ile
1               5                  10

<210> SEQ ID NO 10
<211> LENGTH: 7
<212> TYPE: PRT
<213> ORGANISM: Human immunodeficiency virus type 1

<400> SEQUENCE: 10

Glu Gly Thr Asp Arg Val Ile
1               5

<210> SEQ ID NO 11
<211> LENGTH: 5
<212> TYPE: PRT
<213> ORGANISM: Human immunodeficiency virus type 1

<400> SEQUENCE: 11

Leu Asp Lys Trp Ala
1               5

<210> SEQ ID NO 12
<211> LENGTH: 6
<212> TYPE: PRT
<213> ORGANISM: Human immunodeficiency virus type 1

<400> SEQUENCE: 12

Glu Leu Asp Lys Trp Ala
1               5

<210> SEQ ID NO 13
<211> LENGTH: 7
<212> TYPE: PRT
<213> ORGANISM: Human immunodeficiency virus type 1

<400> SEQUENCE: 13

Glu Leu Asp Lys Trp Ala Ser
1               5

<210> SEQ ID NO 14
<211> LENGTH: 12
<212> TYPE: PRT
<213> ORGANISM: Artificial
```

-continued

```
<220> FEATURE:
<223> OTHER INFORMATION: peptide comprising minimal 2F5-epitope ELDKWA
      of gp41 of HIV-1

<400> SEQUENCE: 14

Gly Gly Gly Leu Glu Leu Asp Lys Trp Ala Ser Leu
1               5                   10

<210> SEQ ID NO 15
<211> LENGTH: 20
<212> TYPE: PRT
<213> ORGANISM: Human immunodeficiency virus type 1

<400> SEQUENCE: 15

Gln Thr Gln Gln Glu Lys Asn Glu Gln Glu Leu Leu Glu Leu Asp Lys Trp Ala
1               5                   10                  15

Ser Leu
     20

<210> SEQ ID NO 16
<211> LENGTH: 17
<212> TYPE: PRT
<213> ORGANISM: Human immunodeficiency virus type 1

<400> SEQUENCE: 16

Gly Cys Ser Gly Lys Leu Ile Cys Thr Thr Ala Val Pro Trp Asn Ala
1               5                   10                  15

Ser

<210> SEQ ID NO 17
<211> LENGTH: 20
<212> TYPE: PRT
<213> ORGANISM: Human immunodeficiency virus type 1

<400> SEQUENCE: 17

Ser Leu Ile Tyr Ser Leu Leu Glu Lys Ser Gln Thr Gln Gln Glu Lys
1               5                   10                  15

Asn Glu Gln Glu
             20
```

IGG1 MONOCLONAL ANTIBODY WITH ANTI-HIV NEUTRALIZING ACTIVITY

TECHNICAL FIELD

The present invention is in the fields of applied microbiology and vaccine development and relates to a cryptic epitope on gp41 of HIV-1 and to synthetic peptides mimicking this cryptic epitope or essential parts thereof and to applications of these peptides for eliciting HIV-1 neutralizing antibodies in mammalian hosts. The invention further relates to the HIV-1 neutralizing antibodies elicited by any one of these peptides and to anti-idiotypic antibodies effective in inhibiting or preventing the action of said HIV-1 neutralizing antibodies.

BACKGROUND

The presence of specific antibodies has been shown to play an important role in the protection against numerous human viral diseases. However, the role of the humoral immune response in HIV infection is still controversial. There are indications that the development of a broad neutralizing immune response, as found in long-term non-progressors, delays disease progression in contrast to rapid disease progressors where neutralizing antibody titers are often low. Other studies have suggested that mothers with high neutralizing antibody titers are less likely to transmit the virus to their newborns. A general correlation between the presence of neutralizing antibodies and disease manifestations was observed. Moreover, a decline in HIV specific antibody responses often predicts a poor diagnosis. Numerous animal and human trials were performed to study the role of antibodies in HIV-1 infection. Infusion of HIV-1 specific neutralizing antibodies to chimpanzees and macaques followed by an intravenous or mucosal challenge with HIV or chimeric simian/human immunodeficiency virus (SHIV) prevented infection or disease progression. Positive effects of passive immunization with monoclonal or polyclonal antibody preparations against HIV-1 were also observed in a number of trials in human volunteers. For example, the two human monoclonal antibodies 2F5 (ECACC Acc. Nr. 90091704) and 2G12 (ECACC Acc.Nr. 93091517) showed beneficial effects in a phase I clinical trial. Repeated infusions of both antibodies to HIV-positive patients resulted in reduction of viral loads and infected peripheral mononuclear cells (PBMC), increase of CD4+ T lymphocytes and complement activation.

So far, the number of monoclonal antibodies recognizing conserved epitopes and known to have a high therapeutic potential is low (D'Souza et al., J Infect Dis 1997; 175:1056-1062). Only the three monclonal antibodies (mAbs) 2F5, 2G12 (Buchacher et al., AIDS Res Hum Retroviruses 1994; 10:359-369), and IgG1b12 (Burton et al., Science 1994; 266: 1024-1027) were reported to display significant cross-clade antiviral activity. The identification of monoclonal antibodies to conserved neutralizing B-cell epitopes on the HIV-1 envelope may not only be valuable for passive immunization strategies but also gives important information for a vaccine design based on the induction of a broad humoral immune response. There are indications that a vaccine based exclusively on T-cell epitopes would most probably not be sufficient to protect against HIV-1 infection (Parren et al., AIDS 1999; 13(suppl A):S137-S162).

Some years ago, we have established a panel of thirty-three human monoclonal antibodies against HIV-1 by immortalization of human peripheral blood lymphocytes from HIV-1 positive donors. Out of this panel two antibodies (2F5, 2G12) were identified to be potent inhibitors of laboratory and primary isolates of HIV-1. MAbs 2F5 and 2G12 were further developed and soon recognized to be two of the most potently neutralizing antibodies. Monoclonal antibody 4E10 (ECACC Acc. Nr. 90091703), originally an IgG3 antibody, was included into an evaluation program of the Antibody Serological Project (ASP) and was shown to neutralize some laboratory strains (D'Souza et al., AIDS 1994; 8:169-181).

BRIEF DESCRIPTION OF THE INVENTION

MAb 4E10 was now cloned in a continuous CHO cell line as an IgG1-class antibody wherein the constant regions of the heavy chains were identical with the ones of recombinant mAbs 2F5 and 2G12. Surprisingly, after this class switch from IgG3 to IgG1, mAb 4E10 showed increased neutralizing potency. Even more so, contrary to expectations the mAb 4E10 in its IgG1 version, but not in its IgG3 version, was the only antibody that neutralized all primary isolates derived from HIV-1 positive individuals participating in a phase I clinical trial with mAbs 2F5 and 2G12. Also, it neutralized primary HIV-1 isolates that were insensitive towards neutraliziation by either or both of mAbs 2F5 and 2G12.

It is therefore an object of the present invention to provide an improved 4E10 antibody of class IgG1 that has a significantly increased HIV-1 neutralizing activity compared to the previously known mAb 4E10 of class IgG3 (ECACC Acc. Nr. 90091703), and which neutralizes primary HIV-1 isolates that are insensitive towards neutraliziation by either or both of mAbs 2F5 and 2G12. It is another object of the present invention to provide for methods of use of the improved IgG1 class mAb 4E10 (hereinafter termed 4E10-IgG1) for diagnostic and therapeutic purposes as well as for eliciting or screening of anti-idiotypic antibodies that are capable of inhibiting or preventing the HIV-1 neutralizing action of mAb 4E10-IgG1. It is yet another object of the present invention to provide for any such anti-idiotypic antibodies that mimic at least an essential part of the 4E10 epitope on gp41, as well as for products, particularly anti-HIV-1 vaccines, containing one or more of those anti-idiotypic antibodies, and for their use.

The term "4E10" as subsequently used herein refers to human monoclonal antibody 4E10 in both the IgG3 and the IgG1 variant, unless expressly stated otherwise. However, in the examples and in the corresponding drawings the term "4E10" typically refers to the IgG1 variant because the experiments disclosed therein have been conducted using the IgG1 variant of 4E10. The term "4E10-IgG3" shall exclusively refer to the known IgG3 variant and the term "4E10-IgG1" to the IgG1 variant of 4E10. Mab 4E10-IgG3 is produced by a hybridoma cell line deposited at ECACC under Accession Nr. 90091703, while 4E10-IgG1 is expressed by a CHO cell line (deposited under the Budapest Treaty at ECACC Acc. Nr. 01110665). Both variants recognize the same epitope on gp41 of HIV-1. They differ significantly, however, in their HIV-1 neutralizing capacity.

It is further disclosed herein that mAb 4E10 recognizes a hitherto unknown epitope on gp41 at a location C-terminal to the 2F5 epitope. The screening of mAb 4E10 against T-cell line adapted (TCLA) HIV-1 isolates and primary HIV-1 isolates of different clades indicates that this antibody may be at least as potent as 2F5 and 2G12 in its neutralizing potential. The in vitro neutralizing properties of 4E10-IgG1 in comparison to other well characterized neutralizing monoclonal antibodies are described herein. It is therefore another object of the present invention to provide synthetic peptides that mimic at least an essential part of the binding epitope located on gp41 of HIV-1 that is recognized by mAb 4E10. It is a further object of the invention to provide for such synthetic peptides in combination with or covalently linked to a suitable immunogenic carrier such as a virus or part of a virus, e.g. a viral protein. It is also an object of the invention to provide for vaccines containing at least one of said synthetic peptides or at least one of said synthetic peptides in combination with or linked to a suitable immunogenic carrier, or at least one anti-idiotypic antibody effective against 4E10, or any combination of said peptides and/or anti-idiotypic antibodies. It is also an object of the present invention to provide for a pharmaceutical composition comprising mAb 4E10-IgG1 in combination with a suitable carrier, and optionally as a mixture with at least one other antibody, preferably selected from the group consisting of 2F5 and 2G12. It is yet another object of the invention to provide for the use of such pharmaceutical compositions and vaccines in the prophylactic or therapeutic treatment of HIV-1 endangered or infected people, and particularly for the prevention or therapy of AIDS.

DETAILED DESCRIPTION OF THE INVENTION

In an evaluation program of the AIDS Clinical Trials Group Antibody Selection Working Group only mAbs 2F5, 2G12, and IgG1b12 were identified to be potent candidates for anti-HIV-1 passive immunotherapy. Our recent findings presented herein show that 4E10-IgG1 is an additional antibody of comparable antiviral potential.

Epitope mapping studies revealed that 4E10 recognizes an epitope on the ectodomain of gp41. As 4E10 did not bind to gp160$_{MN}$ peptide 2030 (QTQQEKNEQELLELDKWASL) (SEQ ID NO: 15). Nor to the GGGLEDKWASL (SEQ ID NO: 14) peptide, it is unlikely that the 2F5 core epitope consisting of the amino acids LDKWA (SEQ ID NO: 11) does essentially contribute to binding of 4E10 to gp160$_{MN}$ peptide 2031 (LLELDKWASLWNWFDITNWL)(SEQ ID NO: 7). Our conclusion that amino acids subsequent to this region are responsible for recognition by 4E10 was confirmed by additional epitope mapping studies, employing peptide libraries for mapping. The results showed that the 4E10 core epitope is indeed located C-terminal to the 2F5 epitope and comprises at least a sequence of 6 amino acids (aa) identical with or corresponding to aa 672-677 (NWFDIT) (SEQ ID NO: 1) of gp41 of TCLA isolate HTLV IIIMN.

The term "corresponding" in this context means that the amino acid sequence of the 4E10 epitope may be identical with the amino acid sequence at gp41 of the HIV-1 isolate explicitly referred to or may deviate therefrom due to the degeneracy of the genetic code or due to variations among different HIV-1 isolates. The deviating sequences must, however, still be representative for the binding motif or epitope recognized by mAb 4E10, e.g., they must be detectable from a library containing gp41 fragments by using 4E10 as a screening tool. For instance, the sequence NWFDIT (SEQ ID NO: 1) at aa 672-677 of gp41 of HTLV IIIMN is equivalent or homolog to the sequence NWFNIT (SEQ ID NO: 2) occurring at the same location of gp41 of isolate HXB2. Further examples of equivalent or homolog sequences comprise but are not limited to SWFGIT (SEQ ID NO: 3), TWFGIT (SEQ ID NO: 4), NWFSIT (SEQ ID NO: 5).

The majority of antibodies induced by gp41 during natural infection is directed against the residues in the vicinity of aa 598-604 and 644-663 (numbering according to HIV-1 HXB2; Xu et al., J Virol 1991; 65:4832-4838). These antibodies do not inhibit viral replication and some may even enhance viral infectivity by complement-mediated mechanisms. So far, mAb 2F5 has been the only described anti-gp41 antibody showing potent cross-clade neutralizing properties. Interestingly, 2F5-like specific antibodies are only rarely found in sera of HIV-1 infected individuals. HIVIG (pooled sera of more than 70 HIV-1 positive donators) do not show significant 2F5-like specific binding to gp160 and/or gp41. The region on gp41 to which 2F5 binds is obviously cryptic to the human immune system during natural infection.

The results described herein for mAb 4E10, another broadly neutralizing antibody to this region on gp41, the epitope of which has now been mapped C-terminal to the 2F5 core epitope, confirms that this region is essential for viral infectivity and replication. As both antibodies bind only weakly to infected cells and free virus but show potent neutralizing activities we suggest a similar mechanism of 2F5 and 4E10 for the inhibition of viral replication. Moreover, the results obtained from syncitia inhibition assays according to which pre-incubation of virus with either of the two antibodies did not improve the antiviral efficacy of 4E10 or 2F5, may strengthen this hypothesis.

Accordingly, in view of the findings that both mAbs, although being highly active entry blockers (neutralizers) of HIV-1, bind only very weakly to free virus and HIV-1 infected cells it is concluded that this fusogenic region on gp41 is only exposed during the event of fusion of the HIV-1 with the host cell. That might on one hand give an additional explanation for the cryptic nature of these neutralizing 2F5 and 4E10 epitopes during natural infection. On the other hand we did so far not find any HIV-1 isolate that was insensitive towards neutralization by a combination of both of these antibodies. This is an important indication that this particular region of the ectodomain of gp41 bears the potential of a highly efficacious anti-HIV-1 remedy if properly presented on a suitable immunogenic carrier or when mimicked by an anti-idiotypic antibody, and makes it a promising candidate for the manufacture of a vaccine for active immunization against HIV-1.

Therefore, in one embodiment the present invention relates to a vaccine for active immunization against HIV-1 infection, which comprises at least one peptide that interferes with HIV-1 entry into target cells and preferably induces an HIV-1 neutralizing immune response, and which peptide is a fragment of gp41 of HIV-1 and comprises an amino acid sequence corresponding to aa 672-677 of gp41 of TCLA isolate HTVL IIIMN. In another embodiment the invention relates to a vaccine that contains at least one of the aforementioned peptides, and/or at least one anti-idiotypic antibody that is reactive with the binding paratope of mAb 4E10, and wherein said antibody mimics a fragment of gp41 of HIV-1 comprising an amino acid sequence corresponding to aa 672-677 of gp41 of TCLA isolate HTVL IIIMN. The vaccine may further comprise a suitable, i.e. pharmaceutically acceptable carrier.

MAb 4E10 inhibits viral replication of TCLA and primary strains of HIV-1 already at rather low concentrations, comparable to the ones applicable hen using 2F5 or 2G12. It exerts similar cross-clade antiviral activity when compared to the other tested mAbs. Although 2F5 and 4E10 recognize adjacent epitopes they do not antagonize each other when tested in combination. 4E10 turned out to be even more efficacious than each of 2F5 and 2G12 against the HIV-1 isolates obtained from asymptomatic HIV patients who participated in a recently performed phase I clinical trial employing mAbs 2F5 and 2G12. On the other hand, 4E10 neutralized only one out of six isolates that were derived earlier from Austrian late-stage AIDS patients. In our current panel of primary isolates there was only one other isolate (92UG029) that was relatively resistant to 4E10. It is noteworthy that these six resistant isolates (i.e., the five earlier obtained resistant isolates and the one current isolate) use CXCR4 as the only one co-receptor for host cell entry. All other isolates that showed macrophage- or dualtropic phenotype were readily inhibited by mAb 4E10. In contrast, all TCLA viruses using CXCR4 for entry were inhibited at low 4E10 concentrations. However, the results obtained with neutralization sensitive TCLA strains in a cell-line based syncitium assay may not be comparable to PBMC based assays with primary viruses.

The development of highly-active antiretroviral therapy (HAART) for HIV-1 infection has dramatically improved the situation of HIV-1 positive individuals, at least in the developed world (Carpenter et al., JAMA 2000; 283:381-390). Nevertheless, severe side effects and the occurrence of HAART resistant viruses generate an urgent need for new therapy approaches acting on additional target sites. The current focus lies on entry-inhibitors, including monoclonal antibodies, antibody-like molecules and peptides. The mAbs 2F5 and 2G12, particularly when used in combination, have already shown remarkable antiviral efficacy in HIV-1 positive volunteers. We therefore provide for additional HIV-1 neutralizing antibodies having the binding characteristics of mAb 4E10.

Accordingly, in one embodiment of the invention there is provided an HIV-1 neutralizing monoclonal antibody other than the published human mAb 4E10-IpG3, wherein said antibody binds to an amino acid sequence corresponding to aa 672-677 (an NWFDIT)(SEQ ID NO: 1) of gp41 of TCLA isolate HTVL IIIMN. In a preferred embodiment this antibody neutralizes even HIV-1 mutants that are insensitive towards neutralization by mAb 2F5 and/or mAb 2G12. One representative of this type of neutralizing antibodies is mAb 4E10-IgG1, i.e., the IgG1 variant of the known mAb 4E10-IgG3.

At this occasion, it is pointed out that some prior art information concerning mAb 4#10-IpG3 was apparently erroneous: Buchacher et al., (AIDS Research and Human Retroviruses 10(4), 1994, 359-369) published results that demonstrate binding of mAb 4E10 to a C-terminal epitope at gp41 amino acid position aa 824-830 (numbering referring to HIV-1 strain Bh10). When repeating their experiments we were unable to confirm such finding. Also, the cross-reaction with MHC class II proteins reported therein was not observed. We did not find any interaction with the relevant peptides 2047 and 2048 containing the amino acids EGTDRVI (SEQ ID NO: 10).

In spite of such misleading information of the prior art rendering mAb 4E10-IgG3 just one out of a number of poorly interesting antibodies with no promising anti-HIV properties, we subjected the antibody once more to comparative inhibition assays after having changed its phenotype from IgG3 to IgG1 by recombinant expression in CHO cells. The results obtained from neutralization experiments with the IgG1 variant were unexpectedly favorable and promising and exceeded our expectations by far, as outlined hereinbefore.

4E1-IgG1 appears to be a powerful tool, e.g. for passive immuniziation, because mAb 4E10-IgG1 was shown to neutralize also viruses that escaped neutralization of either or both of the 2F5 and 2G12 antibodies, and further because we were unable to find any HIV-1 isolate that was insensitive towards neutralization by a combination of 2F5 and 4E10-IgG1. The present invention in one embodiment therefore relates to a pharmaceutical composition for inhibiting or preventing HIV-1 infection of mammalian cells which comprises at least one HIV-1 neutralizing monoclonal antibody that binds to an amino acid sequence corresponding to aa 672-677 of gp41 of TCLA isolate HTVL IIIMN, the most preferred antibody being mAb 4E10-IgG1. In another preferred embodiment, the pharmaceutical composition comprises mAb 4E10-IgG1 in combination with at least one other neutralizing anti-HIV-1 antibody, preferably in combination with at least one of mAbs 2F5 and 2G12.

In still another embodiment the present invention relates to the use of mAb 4E10, optionally in its IgG1 variant, for eliciting or screening for an anti-idiotypic antibody that is reactive with the binding paratope of mAb 4E10 and that mimics the 4E10 epitope or an essential part thereof, i.e., that mimics a fragment of gp41 of HIV-1 comprising an amino acid sequence that corresponds to aa 672-677 of gp41 of TCLA isolate HTVL IIIMN.

In yet another embodiment the present invention relates to an anti-idiotypic antibody that is reactive with the binding paratope of mAb 4E10, wherein said antibody mimics a fragment of gp41 of HIV-1 comprising an amino acid sequence corresponding to aa 672-677 of gp41 of TCLA isolate HTVL IIIMN. Advantageously, the anti-idiotypic antibody mimics a fragment that comprises one or more flanking amino acids on either or both sides of said amino acid sequence corresponding to aa 672-677 of gp41 of TCLA isolate HTVL IIIMN, and wherein said flanking amino acids are present in the same composition and same order as occurring at gp41 of HIV-1. It is preferred that the anti-idiotypic antibody, that can be obtained, for instance, by screening sera of mammalian hosts immunized with 4E10-IgG1, interferes with HIV-1 entry into target cells, particularly at the stage of virus-cell fusion. It is also preferred that the anti-idiotypic antibody induces an HIV-1 neutralizing immune response in vitro as well as in vivo in a mammalian recipient.

Further preferred embodiments of the present invention are laid down in the dependent claims.

In order that the invention described herein may be more fully understood, the following examples are set forth. The examples are for illustrative purposes only and are not to be construed as limiting this invention in any respect.

EXAMPLES

The following materials and methods were used in the subsequent examples 1 to 7:

a) Antibodies

Generation, production and characterization of human monoclonal antibodies 4E10, 2F5, 2G12, and 3D6 have been described previously (D'Souza et al., J Infect Dis 1997; 175: 1056-1062; Kunert et al., Biotechnol Bioeng 2000; 67:97-103). Briefly, antibody producing hybridomas were generated by a combined polyethylene glycol/electrofusion method. PBMC from asymptomatic HIV-1 positive donors were fused with the mouse-human heteromyeloma cell line CB-F7. Hybridoma supernatants were screened for HIV-specific antibody production and positive clones were further analyzed by ELISA, Western blot, and immunofluorescence assays. In order to enable safe mass production and to change the isotype of 2F5 and 4E10 from IgG3 to IgG1 the antibodies were expressed recombinantly in Chinese Hamster Ovary cells (CHO) as IgG1 (k). For the present studies described in the subsequent examples 1-7 the recombinant CHO IgG1 versions of the 2F5 and 4E10 antibodies were used.

4E10, 2F5, and 2G12 contain identical constant regions and differ only in their variable parts which were derived from the original hybridoma clones. 2G12 recognizes a conformation sensitive epitope on gp120, mAb 2F5 recognizes the ELDKWA motif on the ectodomain of gp41, and 4E10 a different epitope on gp41. 3D6 recognizes an eptope in the immunodominant loop of gp41 (amino acids GCSGKLICTAVPWNAS)(SEQ ID NO: 16) and served as a non-neutralizing control in all syncitium inhibition assays.

The human mAb IgG1b12 was kindly provided by Dr. Dennis Burton, The Sripps Research Institute. Its generation was described in Burton et al., Science 1994; 266:1024-1027. IgG1b12 recognizes an epitope overlapping the CD4 binding domain and was shown to inhibit CD4/gp120 interaction. HIVIG was prepared by NABI (Boca Raton, Fla., USA) and contained purified polyclonal HIV-1 specific immunoglobulin derived from multiple HIV-1 positive patients. The preparation containing 98% monomeric IgG was kindly provided by Dr. John Mascola.

b) Cells

The AA-2 cell line for the syncitium inhibition assay was obtained from the NIH AIDS Reagent Reference Program (provided by M. Hershfield). Cells were passaged twice weekly in cell culture medium (CCM) containing RPMI-1640 (Biochrom, Berlin, Germany) supplemented with 10% heat-inactivated FCS and 4 mM L-glutamine.

PBMC for virus neutralization assays were obtained by Ficoll gradient centrifugation at 400 *g of blood derived from HIV negative volunteers. Cells were stimulated with phytohemagglutinin (Sigma, St. Louis, Mo.) in CCM supplemented with 20 U/ml IL-2 and antibiotics (Penicillin 100 U/ml, Streptomycin 100 µg/ml; Biochrom, Berlin, Germany) for two days before use.

c) Viruses

HIV-1 primary isolates 92BR021/030, 92RW009/021, 92TH14/21/24, and 92UG001/029/037 were obtained from the WHO Network for HIV Isolation and Characterization and provided by the MRC AIDS Reagent Project. Viruses WYG, WRF, WHM, WRB, and WSC were isolated earlier from Austrian late-stage AIDS patients. Isolates designated S2/02, S2/03, S2/04, S2/05, S2/06, S2/08, S2/09, and P6/71 were isolated during the 1999/2000 phase I clinical trial with 2F5 and 2G12 from asymptomatic HIV-1 positive volunteers. Viruses were grown on stimulated PBMC and tested as cell free supernatants.

TCLA viruses HTLV-IIIB, HTLV-IIIMN, and HTLV-II-IRF were derived from infected H9 cells provided by the American Type Culture Collection and the NIH AIDS Research and Reference Reagent Program; cl82 was provided by Dr. E. M. Fenybö. Stocks were grown and titrated on AA-2 cells. The 50% tissue culture infectious dose (TCID50) was calculated according to the method of Reed and Muench (Reed L J and Muench H; AM J Hygiene 1938; 27:493-497).

Example 1

Epitope Mapping by ELISA

For mapping of the 4E10 epitope, thirty-four overlapping gp41 peptides of HTLV-IIIMN (aa 501-856, Table 1) produced by AnaSpec, Incorporated, were derived from the AIDS Research and Reference Reagent Program (numbers 2015-2049). Most of these peptides were twenty amino acids in length with ten amino acid overlaps between sequential peptides. The peptide GGGLELDKWASL (SEQ ID NO: 14) was synthesized in-house.

The truncated E. coli recombinant gp41 MN peptide was provided by Dr. J. Raina through the NIBSC Centralised Facility for AIDS Reagents. Vaccinia-recombinant gp160IIIB was a gift from the Immuno-AG, Austria. Microtiter plates (Nunc Maxisorp, Roskilde, Denmark) were coated overnight at +4° C. with synthetic peptides, gp41 MN, or gp160IIIB at a constant concentration of 1 µg/ml or serial dilutions, starting with 10 µg/ml, in 0.1 M sodium carbonate buffer. Plates were washed with PBS containing 0.1% Tween 20 and blocked with 2% skim milk for 2 hours at 37° C. After washing, serial dilutions of 4E10 or 2F5 (starting with 500 ng/ml) or constant concentrations (100 ng/ml) were incubated for one hour. Plates were washed and incubated with goat anti-human IgG(g) conjugated with horseradish peroxidase (Zymed, San Francisco, Calif.) for 1 hour at RT. Plates were washed and developed with 1,2-o-phenylenediamine dihydrochloride (OPD; Sigma, St. Louis, Mo.) staining solution containing 0.03% H2O2. After stopping the reaction with 2.5 N H2SO4 the optical density (OD) was measured at 492/620 nm.

For competition studies, all overlapping gp41MN peptides, GGGLELKDWASL (SEQ ID NO: 14), were pre-incubated with serial dilutioins of peptides (starting with 50 µg/ml for synthetic peptides and 5 µg/ml for gp41) for 2 hours at 37° C. before addition to plates coated with peptide 2031 or gp41 (1 µg/ml).

Immunofluorescence analysis by confocal microscopy and flow cytometry For confocal microscopy, PBMC infected with primary HIV-1 viruses (S2/02, S2/04, S2/08) were allowed to adhere to slides (Biorad, München, Germany) for 1 hour at 37° C. Uninfected non-stimulated and mitogen-stimulated PBMC of the same donor served as negative controls. Slides were washed with PBS and blocked with 5% skim milk in PBS for 20 minutes. Antibodies 4E10, 2F5, 2G12, and HIVIG were applied at concentrations of 100 µg/ml and incubated for 1 hour at +4° C. Cells were washed with PBS/skim milk and incubated with FITC labeled polyclonal goat anti-human IgG(g)(Sigma, St. Louis, Mo.) for one hour. After intensive washing with PBS, cells were fixed with paraformaldehyde (3%) for 20 minutes and subsequently 
washed with PBS. The fluorescence signal was visualized in a Biorad MRC 600 confocal microscope.

Alternatively, the same experiments were performed with paraformaldehyde fixation before staining of PBMC and incubation steps at 37° C.

For flow cytometric analysis, HIV-1 infected PBMC (isolates S2/02, S2/04), uninfected PHA-P stimulated and unstimulated cells were washed and blocked with PBS containing 10% FCS for 30 minutes at +4° C. PBMC were incubated with 4E10, 2F5, and HIVIG (100 µg/ml) for one hour on ice. After washing with PBS/FCS cells were incubated with polyclonal FITC-labeled goat anti-human IgG(g) for 1 hour, again on ice. Cells were washed with PBS and fixed with 3% paraformaldehyde for 1 hour at room temperature before analysis on a FACS-Vantage (Becton Dickinson, San Jose, Calif.).

Syncitium Inhibition Assay

Syncitium inhibition was assessed using AA-2 cells as indicator cell line with syncitium formation as read-out as described previously (Purtscher et al., AIDS Res Hum Retroviruses 1994; 10:1651-1658). Briefly, serial dilutions of antibodies in polybrene containing CCM (5 µg/ml; Sigma, St. Louis, Mo.) were pre-incubated with virus of 102-103 TCID50/ml for 1 h at. 37° C. before addition of AA-2 cells. Cells were incubated for 5 days before assessment of syncitium formation. Experiments were performed with 4-8 replicates per dilution step. The presence of at least one syncitium per well was considered as indication for HIV-1 infection. The 50% inhibiting concentration (IC50) was calculated according to the method of Reed and Muench, AM J Hygiene 1938; 27:493-497. Experiments were performed with 2F5, 2G12, and 4E10. All assays included a virus titration of the inoculum to confirm the infectious titer. In alternative experiments, the pre-incubation step of antibody and virus was omitted.

Neutralization Assay

The neutralizing activity of hu-mAbs 4E10 (=4E10-IgG1), 2F5 (2F5-IgG1), 2G12, and IgG1b12 was determined in a PBMC based neutralization assay as described previously (Purtscher et al., AIDS Res Hum Retroviruses 1994; 10:1651-1658). Serial dilutions of antibodies were pre-incubated with virus for 1 h at 37° C. before addition of PBMC and further incubation of 7 days. Experiments were performed with 4 replicates per dilution step. Virus growth was measured by a sensitive p24-ELISA (Steindl et al., J Immunol Methods 1998; 217:143-151) at the time point of assay termination. The ratios of p24 antigen production in mAb-containing cultures to p24 antigen production in control cultures, taking into account input p24, were calculated and mAb concentrations (µg/ml) causing 50% inhibition were determined by linear regression analysis. Each assay included a virus titration to determine the actual TCID50. Tests were considered to be valid when viral titers were between 102-103 TCID50 and maximum replication resulted in at least fivefold higher p24 concentrations than input p24.

Determination of Synergy of mAb Combinations

Calculation of synergistic neutralizing effects of mAbs in combinations was determined according to the method of Chou-Talalay (Chou T C and Talalay, Adv Enzyme Regul 1984; 22:27-55). Briefly, the amount of single mAbs necessary to achieve 50% inhibition was compared to the concentrations required when a combination of mAbs was used. The combination index (CI) was calculated based on the equation CI=(D1)/(Dx)1+(D2)/(Dx)2. (Dx)1 and (Dx)2 are the concentrations of mAb1 and mAb2 alone required to achieve 50% neutralization whereas (D1) and (D2) are the doses of mAb1 or mAb2 when used in combination. CI<1 indicates synergism, CI=1 additive effects and CI>1 antagonism.

Figure 1:
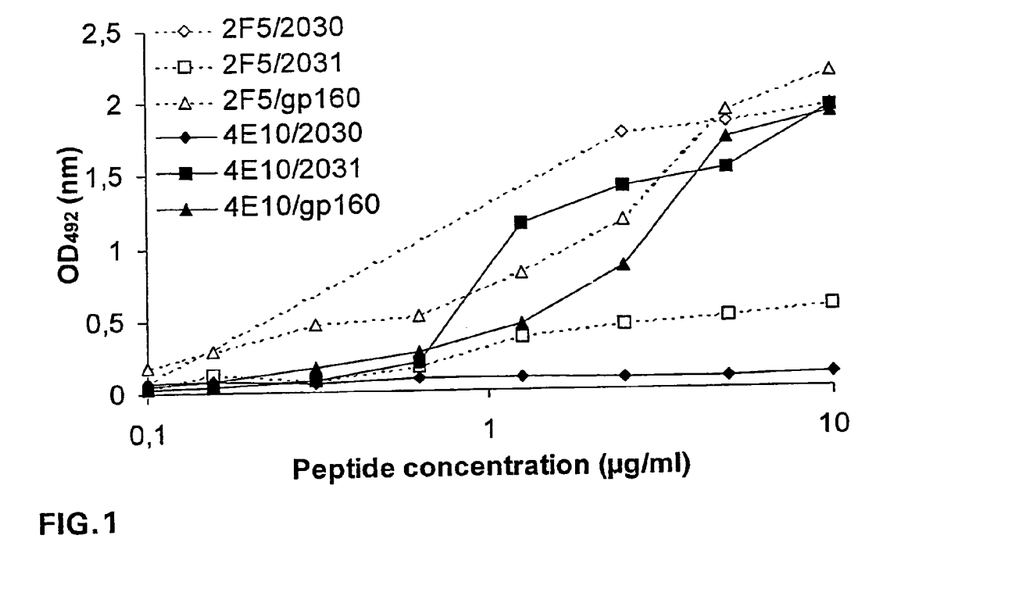
FIG. 1: Binding of 2F5 and 4E10 to peptides 2030, 2031, and gp160$_{IIIB}$. Serial twofold dilutions of peptides were coated overnight on ELISA plates before incubation with constant amounts of 4E10 or 2F5 (100 ng/ml). Binding was detected with goat anti-human IgG(γ) conjugated with horseradish peroxidase.

Results:

To determine the binding region of 4E10, thirty-four (34) overlapping gp41MN peptides were tested for their reactivity with 4E10 by ELISA. The peptide GGGLELDKWASL (SEQ ID NO: 14) comprising the minimal 2F5 gp41-epitope was used as negative control, gp41MN and gp160IIIB served as positive controls. 2F5 was tested in parallel to explore the possibility that both antibodies recognize the same epitope. 4E10 bound to peptide 2031, gp160 (FIG. 1 and Table 1) and gp41 in a dose dependent manner. No other peptide showed significant reactivity with 4E10. 2F5 bound to the same peptides and additionally to peptide 2030 (FIG. 1 and Table 1) and the GGGLELDKWASL peptide (SEQ ID NO: 14), which all contain the ELDKWA (SEQ ID NO: 12) sequence.

TABLE 1

Amino acid sequences of overlapping HIV-1 gp41 MN-peptides used for 4E10 and 2F5 ELISA binding studies[4]

| Sequence | Code | Region | 4E10 binding | 2F5 binding |
|---|---|---|---|---|
| n.p. | 2015-2028 | 501-650 | − | − |
| SLIYSLLEKSQTQQEKNEQE (SEQ ID NO: 17) | 2029 | 641-660 | − | − |
| QTQQEKNEQELLELDKWASL (SEQ ID NO: 15) | 2030 | 651-670 | − | + |
| LLELDKWASLWNWFDITNWL (SEQ ID NO: 7) | 2031 | 661'-680 | + | + |
| DITNWLWYIKI (SEQ ID NO: 9) | 2032 | 675-685 | − | − |
| n.p. | 2034-2049 | 696-856 | − | − |

Figure 3A:
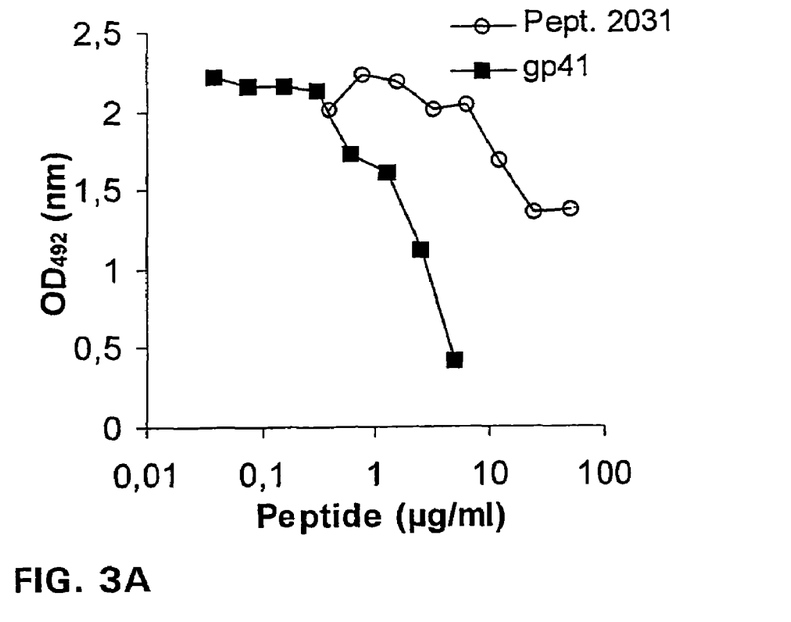
FIGS. 3A, B: Inhibition of binding of mAb 4E10 to ELISA plates pre-coated with (A) gp41 or (B) peptide 2031 after pre-incubation of mAb 4E10 with either gp41 or peptide 2031. Serial twofold dilutions of peptides gp41 or 2031 were pre-incubated with constant amounts of 4E10 (250 ng/ml) before addition to the gp41 or peptide 2031 coated plates. Binding of antibody was detected with goat anti-human IgG (γ) conjugated with horseradish peroxidase.
Figure 3B:
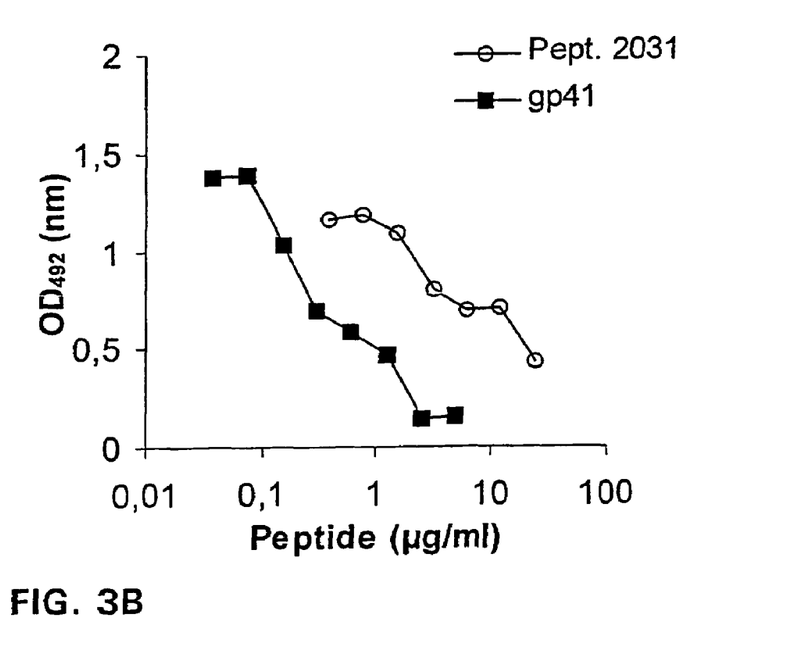

[4]Binding of 4E10 and 2F5 to synthetic peptides coated to ELISA plates was detected with goat anti-human IgG(g).
n.p. not presented Competition studies performed with all synthetic gp41 MN peptides and gp41 confirmed that only peptide 2031 and gp41 (gp160 was not tested) reacted with 4E10. Pre-incubation of constant amounts of 4E10 with serial dilutions of peptide 2031 and gp41 only resulted in a dose dependent inhibition of binding of mAb 4E10 to gp41 (FIG. 3A) or to peptide 2031 (FIG. 3B). No other peptide could inhibit binding of 4E10.

From the above results we concluded that the minimum binding epitope (core epitope) of 4E10 was entirely present on peptide 2031 and is located subsequent to the ELDKWAS (SEQ ID NO: 13) epitope of 2F5 and within the aa sequence LWNWFDITNWL (SEQ ID NO: 6)(aa positions 670-680 of gp41; numbering according to TCLA isolate HTLV-IIIMN). More detailed mapping using smaller peptides revealed a core epitope of six amino acids comprising the aa sequence NWFDIT (SEQ ID NO: 1)(aa 672-677 of gp41 of HTLV IIIMN). Flanking amino acids on either or both sides of that hexamer amino acid sequence may, however, be advantageous for achieving best neutralization efficacy when using this core epitope in the form of a synthetic peptide, preferably in combination with or linked to a suitable immunogenic carrier, for immunization purposes.

It is therefore an object of the present invention to provide such synthetic peptides that interfere with HIV-1 entry into target cells and that preferably also induce an HIV-1 neutralizing immune response in vitro and in a mammalian host in vivo, and wherein any such peptide is a fragment of gp41 of HIV-1 and comprises an amino acid sequence corresponding to aa 672-677 of gp41 of TCLA isolate HTVL IIIMN.

In one embodiment the synthetic peptide of the present invention comprises one or more flanking amino acids on either or both sides of that amino acid sequence, wherein the flanking amino acids are present in the same composition and same order as occurring at gp41 of HIV-1. It is preferred that the synthetic peptides of the present invention are composed of no more than 23 amino acids. It is also preferred that said one or more flanking amino acids are present in the same composition and the same order as occurring at gp41 of HIV-1 at a location corresponding to aa 658-680 (EQELLELDK-WASLWNWFDITNWL)(SEQ ID NO: 8) of gp41 of TCLA isolate HTVL IIIMN.

Both, the core and the extended core epitopes of 4E10, i.e. synthetic peptides comprising an amino acid sequence identical with or corresponding to (by homology) any one amino acid sequence selected from the group consisting of NWFDIT (SEQ ID NO: 1), SWFGIT (SEQ ID NO: 3), TWFGIT (SEQ ID NO: 4), NWFSIT (SEQ ID NO: 5), LWNWFDITNWL (SEQ ID NO: 6), LLELDKWASLWNWFDITNWL (SEQ ID NO: 7), EQELLELDKWASLWNWFDITNWL (SEQ ID NO: 8), as well as any peptide having an aa sequence in between the core and the extended core epitope may be used for the manufacture of an anti-HIV-1 vaccine as well as for eliciting and screening anti-idiotypic antibodies against mAb 4E10. It is emphasized, however, that minor alterations in any one of these as sequences due to the degeneracy of the genetic code or due to variations between different HIV-1 isolates are also encompassed within the scope of the above-mentioned peptides of the core and extended core epitopes of mAb 4E10.

Additionally, according to another preferred embodiment the synthetic peptides of the present invention are combined with a suitable immunogenic carrier. It is particularly preferred that they are covalently linked to a virus or a viral protein such as, for instance, influenza virus or influenza-virus hemagglutinin. Other carriers, particularly viral envelope proteins, may also be suitable.

Example 2

Immunofluorescence Analysis of 4E10 Binding Characteristics

To study the interaction of 4E10 with HIV-1 antigens present on the surface of infected PBMC and also a possible cross-reactivity with MHC class II, which had been reported previously (Buchacher et al., see above), we performed binding studies of 4E10 to unstimulated and to PHA-P stimulated HIV-1 negative as well as HIV-1 infected PBMC. The binding of 4E10 was compared to that of 2F5, 2G12, and HIVIG by indirect immunofluorescence using confocal microscopy and flow cytometry.

Significant binding was only detected to infected cells where 2G12 and HIVIG bound strongly and 4E10 and 2F5 displayed only weak reactivity (data not shown). Also, 4E10 did not bind any stronger to uninfected PBMC than did 2F5, 2G12, and HIVIG. No difference was observed between the results obtained for native cells stained at +4° C. compared to pre-fixed cells stained at 37° C.

Example 3

Syncitium Inhibition Assay with T-Cell Line Adapted (TCLA) HIV-1 Strains

The capacity of the human monoclonal antibody 4E10 (=4E10-IgG1) to inhibit formation of syncitia by TCLA isolates HTLVIIIB, HTLVIIIRF, HTLVIIIMN, and cl82 in AA-2 cells was compared to the corresponding capacity of mAbs 2F5 and 2G12. MAb 2G12 recognizes a conformation-sensitive, glycosylation dependent epitope on gp120 unrelated to the V1, V2, and V3 loop or the CD4-binding site (Trkola et al., J Virol 1996; 70:1100-1108). 4E10 and 2F5 inhibited syncitium formation for all four viruses whereas 2G12 did not neutralize HTLV-IIIMN (Table 2).

TABLE 2

Syncitium inhibition assay[a] with mAbs 4E10, 2F5, and 2G12 against T-cell line adapted viruses

| Isolate | Clade (gag/env) | Coreceptor (Phenotype) | IC$_{50}$ (µg/ml)[b] | | | |
|---|---|---|---|---|---|---|
| | | | 4E10 | 2F5 | 2G12 | 3D6 |
| IIIB | B/B | X4 (SI) | 1.0 | 0.3 | 0.4 | >50 |
| MN | B/B | X4 (SI) | 0.3 | 0.9 | >50 | >50 |
| RF | B/B | X4 (SI) | 12.5 | 4.4 | 2.4 | >50 |
| cl82 | B/B | X4 (SI) | 6.3 | 0.3 | 3.7 | >50 |

[a]Assays were performed on AA-2 cells using presence or absence of syncitium formation as read-out.
[b]Antibody concentration which inhibited 50% of viral replication SI syncitium inducing 3D6, a mAb recognizing an epitope in the immunodominant loop of gp41 (Buchacher et al. see above), served as a non-neutralizing control and was not able to inhibit syncitium formation. The 50% inhibitory concentrations of 4E10 ranged from 0.3 µg/ml for the MN strain to 12.5 µg/ml for the RF strain. 2F5 and 2G12 neutralized the TCLA strains at comparably low concentrations, except that 2G12 did not neutralize the HTLV-IIIMN virus. 4E10 was the most potent mAb against HTLVIIIMN, 2F5 against HTLVIIIB and cl82 (0.3 µg/ml) whereas 2G12 neutralized HTLVIIIRF at lower concentrations than the two other mAbs (2.4 µg/ml).

Example 4

Influence of Pre-Incubation of Virus and mAb on Syncitia Inhibition

To determine the influence of pre-incubation of virus with antibody before addition to target cells, assays were alternatively performed without the pre-incubation step. Virus (HTLVIIIRF) and mAbs (4E10, 2F5, 2G12) were added simultaneously to AA-2 cells. For 4E10 (-IgG1) and 2F5. (-IgG1) the results did not differ with and without pre-incubation whereas for 2G12 a dramatic increase of 300% was observed after the one-hour pre-incubation step.

Example 5

Neutralization of Primary HIV-1 Isolates

Next, the neutralizing activity of mAb 4E10 (-IgG1) was compared to the corresponding activity of 2F5, 2G12, and IgG1b12 against a panel of primary isolates of different clades in a PBMC based neutralization assay. IgG1b12 binds to a discontinuous epitope that overlaps the CD4-binding domain on gp120 (see Burton et al., Science 1994; 266:1024-

1027). MAb concentrations where 50% neutralization was achieved, are shown in Table 3 (values obtained from two independent experiments).

TABLE 3

Neutralization of primary HIV-1 isolates by mAbs 4E10, 2F5, 2G12 and IgG1b12[a]

| Isolate | Clade (gag/env) | Corecceptor (Phenotype) | IC$_{50}$ (μg/ml)[b] | | | |
|---|---|---|---|---|---|---|
| | | | 4E10 | 2F5 | 2G12 | IgG1b12 |
| 92RW009 | C/A | R5X4 (SI) | 0.6 | 0.3 | 0.1 | n.d. |
| 92RW021 | —/A | R5 (—) | 0.3 | 0.7 | 0.1 | n.d. |
| 92UG029 | A/A | X4 (SI) | 43.4 | 4.9 | <0.1 | n.d. |
| 92UG037 | A/A | R5 (NSI) | 0.4 | 0.7 | 0.1 | n.d. |
| 92TH014 | B/B | R5 (NSI) | 1.0 | 2.6 | 0.1 | n.d. |
| 92BR021 | B/B | R5 (NSI) | 2.7 | 2.7 | >50 | n.d. |
| 92BR030 | B/B | R5 (NSI) | 0.5 | 5.0 | 0.5 | n.d. |
| 92UG001 | D/D | R5X4 (SI) | 4.8 | 6.9 | >50 | n.d. |
| 92TH021 | —/E | R5 (NSI) | 0.5 | 1.1 | >50 | n.d. |
| 92TH024 | A/E | R5 (—) | 3.0 | <0.1 | >50 | n.d. |
| WYG | n.d. | X4 (SI) | >50 | 0.8 | 0.5 | n.d. |
| WRF | n.d. | X4 (SI) | >50 | 4.7 | 4.6 | n.d. |
| WHM | n.d. | X4 (SI) | >50 | 2.1 | 0.6 | n.d. |
| WRB | n.d. | X4 (SI) | >50 | 5.4 | 1.5 | n.d. |
| WSC | n.d. | X4 (SI) | 30.0 | >50 | 0.4 | n.d. |
| S2/02 | n.d. | R5 (NSI) | 10.0 | 8.0 | >50 | 26.6 |
| S2/03 | n.d. | R5 (NSI) | 0.3 | 0.3 | >50 | >50 |
| S2/04 | n.d. | R5 (NSI) | 2.5 | 0.5 | >50 | n.d. |
| S2/05 | n.d. | R5 (NSI) | <0.1 | 0.2 | <0.1 | 0.1 |
| S2/06 | n.d. | R5 (NSI) | 1.2 | 3.5 | >50 | 33.2 |
| S2/08 | n.d. | R5 (NSI) | <0.1 | 1.5 | >50 | 2.0 |
| S2/09 | n.d. | R5X4 (SI) | <0.1 | >50 | <0.1 | <0.1 |

Figure 2:
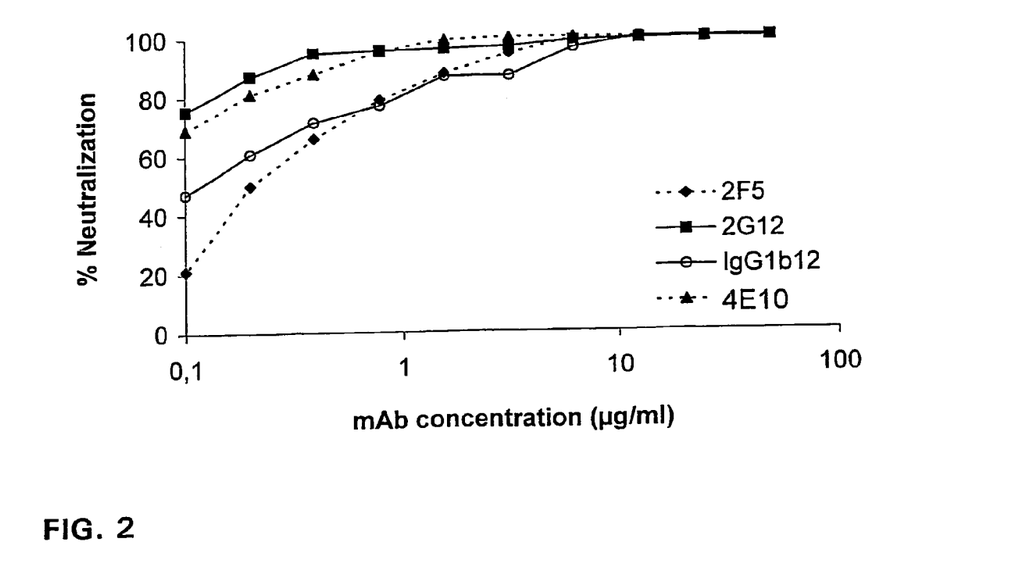
FIG. 2: Neutralization of primary isolate S2/05 by 2F5, 2G12, 4E10, and IgG1b12. The assay was performed on PBMC using p24 production as replication marker. The amount of p24 in culture without mAb was 195 ng/ml.

[a]The assays were performed on mitogen stimulated PBMC using p24 as replication marker.
[b]Antibody concentration which inhibited 50% of viral replication
n.d. not determined
SI syncitium inducing
NSI non-syncitium inducing 4E10 neutralized 18/22, 2F5 20/22, 2G12 13/22, and IgG1b12 5/6 tested isolates at concentrations below 50 μg/ml. For example, 4E10 was as active as 2G12 against isolate S2/05 and more active than 2F5 and IgG1b12 (FIG. 2). Mean concentrations necessary to achieve 50% inhibition of viral replication were 5.7 (4E10), 2.6 (2F5), 0.7 (2G12), and 12.4 μg/ml (IgG1b12) for the neutralized viruses. No virus was resistant to all four antibodies. Moreover, each virus was neutralized by at least one of the anti-gp41 antibodies 4E10 or 2F5, wherein 16/22 isolates were neutralized by both mAbs, 2/22 solely by 4E10 and 4/22 solely by 2F5.

Example 6

Comparison of Neutralization Activity of Hybdridoma mAb 4E 10-IgG3 and CHO Recombinant mAb 4E 10-IgG 1

PBMC based neutralization assay was carried out with primary HIV-1 isolates (see Example 5).

TABLE 4

Neutralization activity of 4E10-IgG3 vs 4E10-IgG1

| Isolate | Clade | 90% Neutralization IgG3 | 90% Neutralization IgG1 | x-fold increase |
|---|---|---|---|---|
| 92UG037 | A | 3.08 | 0.67 | 4.6 |
| 92TH024 | E | 4.48 | 0.31 | 14.5 |
| 92RW009 | A | 8.64 | 2.46 | 3.3 |
| 92BR021 | B | 8.80 | 2.14 | 4.1 |

The results impressively demonstrate the remarkable increase in neutralization efficacy of mAb 4E10-IgG1 over known mAb 4E10-IgG3.

Example 7

Combined Application of mAbs 4E10 and 2F5

Figure 4A:
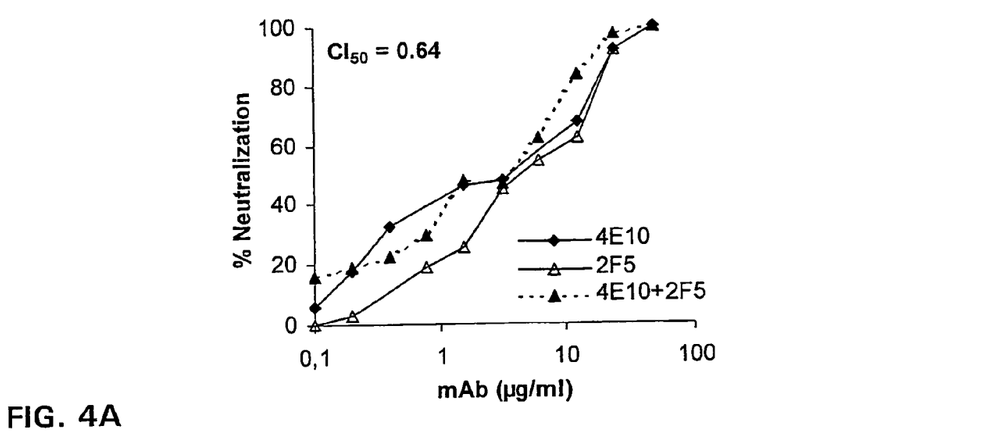
FIGS. 4A, B, C. Neutralization of primary isolate P6/71 by 4E10, 2F5, 2G12, IgG1b12, and double combinations (1:1). The combination indices at 50% neutralization (CI$_{50}$) are indicated. The assay was performed on PBMC using p24 production as replication marker. The amount of p24 in culture without mAb was 96 ng/ml. Synergy was determined by the method of Chou-Talalay where a CI<1 indicates synergy.
Figure 4B:
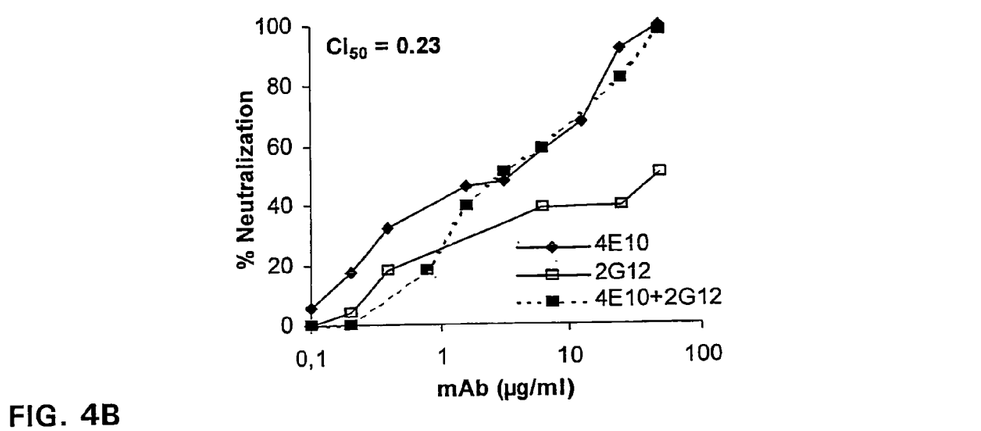
Figure 4C:
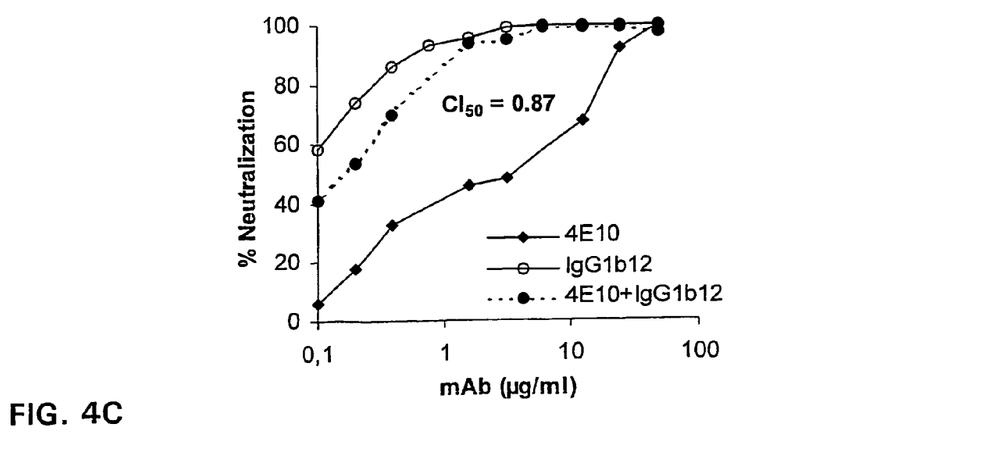

As 4E10 and 2F5 recognize adjacent epitopes, the possible inhibitory inter-action of 2F5 and 4E10 in neutralization of primary viruses was studied for 5 different primary viruses (S2/02, S2/03, S2/04, S2/06, and S2/08) by comparing preparations containing either 2F5 or 4E10 antibodies with a preparation containing a combination (1:1 ratio) of the two antibodies. The combination of 2F5 (-IgG1) and 4E10 (-IgG1) resulted in a slightly synergistic or additive effect (CI≦1) in all experiments; in none of the experiments an antagonistic effect was detected. Results of an additional experiment with the primary isolate P6/71, where 2G12 and IgG1b12 were also included, are shown in FIGS. 4A, 4B, and 4C. Combination indices (CI50) for this experiment were 0.64, 0.23, and 0.87 for the combination of 4E10 with 2F5, 2G12, and IgG1b12, respectively, and indicate that also 2G12 and IgG1b12 do not antagonize 4E10 but rather show additive if not synergistic effects.

Allocation of amino acid sequences:

```
SEQ ID NO: 01    NWFDIT

SEQ ID NO: 02    NWFNIT

SEQ ID NO: 03    SWFGIT

SEQ ID NO: 04    TWFGIT

SEQ ID NO: 05    NWFSIT

SEQ ID NO: 06    LWNWFDITNWL

SEQ ID NO: 07    LLELDKWASLWNWFDITNWL

SEQ ID NO: 08    EQELLELDKWASLWNWFDITNWL

SEQ ID NO: 09    DITNWLWYIKI

SEQ ID NO: 10    EGTDRVI

SEQ ID NO: 11    LDKWA

SEQ ID NO: 12    ELDKWA

SEQ ID NO: 13    ELDKWAS

SEQ ID NO: 14    GGGLELDKWASL

SEQ ID NO: 15    QTQQEKNEQELLELDKWASL

SEQ ID NO: 16    GCSGKLICTTAVPWNAS

SEQ ID NO: 17    SLIYSLLEKSQTQQEKNEQE
```

We claim:

1. An isolated and purified human immunodeficiency virus type 1 (HIV-1) neutralizing monoclonal antibody (mAb) consisting of mAb 4E10-IgG1, produced by a Chinese Hamster Ovarian (CHO) cell line having the ECACC Acc. No. 01110665.

2. A composition comprising the HIV-1 neutralizing monoclonal antibody according to claim 1, and a pharmaceutically acceptable carrier.

3. A method for the preparation of a composition comprising the HIV-1 neutralizing antibody according to claim 1 comprising the following steps:
   a) growing and amplifying the CHO cell line ECACC Acc. No. 01110665 under suitable conditions that result in expression of mAb 4E10-IgG1;
   b) isolating and purifying mAb 4E10-IgG1 from the culture supernatant produced in step (a); and
   c) conjugating said mAb 4E10-IgG1 with a pharmaceutically acceptable carrier.

4. An in vitro or in vivo method for the inhibition of HIV-1 viral replication in mammalian cells by administering a composition comprising the mAb 4E10-IgG1 of claim 1.

5. The composition according to claim 2, further comprising an antibody selected from the group consisting of:
   mAb 2F5, produced by the hybridoma having the ECACC Acc. No. 90091704, and
   mAb 2G12, produced by the hybridoma having the ECACC Acc. No. 93091517.

6. The method of claim 3, wherein step (c) further comprises conjugating at least one of mAb 2F5, produced by a hybridoma having the ECACC Acc. No. 90091704, and mAb 2G12, produced by a hybridoma having the ECACC Acc. No. 93091517 with said mAb 4E10-IgG1 and the pharmaceutically acceptable carrier.

7. The method of claim 4, wherein said mammalian cells are insensitive towards neutralization by either or both of mAb 2F5, produced by a hybridoma having the ECACC Acc. No. 90091704, and mAb 2G12, produced by a hybridoma having the ECACC Acc. No. 93091517.

8. The method of claim 4, wherein said composition further comprises at least one of mAb 2F5, produced by a hybridoma having the ECACC Acc. No. 90091704, and mAb 2G12, produced by a hybridoma having the ECACC Acc. No. 93091517.

9. The method of claim 4, wherein said composition further comprises a pharmaceutically acceptable carrier.

10. The method of claim 8, wherein said composition further comprises a pharmaceutically acceptable carrier.

* * * * *